United States Patent [19]

Gaffar

[11] 4,123,512

[45] Oct. 31, 1978

[54] ANTIBACTERIAL ORAL COMPOSITION

[75] Inventor: Abdul Gaffar, Somerset, N.J.

[73] Assignee: Colgate-Palmolive Company, New York, N.Y.

[21] Appl. No.: 790,782

[22] Filed: Apr. 25, 1977

Related U.S. Application Data

[62] Division of Ser. No. 629,749, Nov. 7, 1975, Pat. No. 4,042,679.

[51] Int. Cl.$^2$ .......................... A61K 7/16; A61K 7/22
[52] U.S. Cl. ........................ 424/54; 424/52; 424/57
[58] Field of Search ...................... 424/49–58

[56] References Cited

U.S. PATENT DOCUMENTS

| | | | |
|---|---|---|---|
| 3,429,963 | 2/1969 | Shedlovsky | 424/56 |
| 3,934,002 | 1/1976 | Haefele | 424/54 |
| 3,937,805 | 2/1976 | Harrison | 424/52 |
| 3,956,480 | 5/1976 | Dichter et al. | 424/54 |
| 3,959,458 | 5/1976 | Agricola et al. | 424/52 |
| 4,025,616 | 5/1977 | Haefele | 424/52 |
| 4,042,679 | 8/1977 | Gaffar | 424/54 |

FOREIGN PATENT DOCUMENTS 2,156,491 5/1972 Fed. Rep. of Germany.
2,159,507 7/1973 France.
2,280,362 2/1976 France.

OTHER PUBLICATIONS

Chem. Abstracts 77 #66118r (1972) of Ger. Offen. 2,156,491 May 31, 1972, "Sodium Polyethylene Polyphosphonates for Dentifrices".
Chem. Abstracts 80 #30710a (1974) of Fr. Demande 2,159,507, Jul. 27, 1973, "Tartar-Retarding Toothpastes Containing Polyamine Polyphosphonates".
Chem. Abstracts 85 #130545x (1976) of Fr. Demande 2,280,362, Feb. 27, 1976, "Tartar-Retarding Toothpastes Containing Polyamine Polyphosphonates".
Anbar et al., Chem. Abstracts 82 #164761t (1975), 82 #25739d (1975), 82 #35008d (1975), "Organic Polymeric Polyphosphonates as Potential Preventive Agents of Dental Caries".

*Primary Examiner*—Shep K. Rose
*Attorney, Agent, or Firm*—Robert L. Stone; Murray M. Grill; Herbert S. Sylvester

[57] ABSTRACT

An antibacterial oral composition effective to promote oral hygiene containing an antibacterial antiplaque agent and an additive which reduces staining of dental surfaces without substantially diminishing the antibacterial and antiplaque activity of the agent. Bis-biguanido hexanes, such as chlorhexidine and alexidine, and quaternary ammonium salts, such as benzethonium chloride and cetyl pyridinium chloride, are typical examples of antibacterial agents. The antistain additive is a polymeric polyphosphonic compound, such as polyallyl bis-(phosphonomethylene) amine acid and salts thereof.

9 Claims, No Drawings

ANTIBACTERIAL ORAL COMPOSITION

This is a divisional of application Ser. No. 629,749 filed Nov. 7, 1975, now U.S. Pat. No. 4,042,679, issued Aug. 16, 1977.

This invention relates to an antibacterial oral composition which promotes oral hygiene.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology 2nd edition (Vol. 2, p. 632-635), incorporated herein by reference. Cationic materials which possess antibacterial activity (i.e. are germicides) are used against bacteria. As bacteria are present in the oral cavity and lead to plaque formation, cationic antibacterial agents have been used in oral compositions to counter plaque formation.

Among the most common of these antibacterial antiplaque quaternary ammonium compounds is benzethonium chloride, also known as Hyamine 1622 or di-iso butyl (phenoxyethoxyethyl dimethyl benzyl ammonium chloride). In an oral preparation this material is highly effective in promoting oral hygiene by reducing formation of dental plaque and calculus. Reduction of plaque and calculus is generally accompanied by reduction in caries formation. Other cationic antibacterial agents of this type are those mentioned, for instance, in U.S. Pat. Nos. 2,984,639; 3,325,402; 3,703,583; and 3,431,208 and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis (2-ethylhexyl)-5-methyl hexa hydro-pyrimidine are typical quaternary ammonium antibacterial agents.

Other types of cationic antibacterial agents which are desirably incorporated in oral compositions to promote oral hygiene by reducing plaque formation are the amidines such as the substituted guanidines e.g. chlorhexidine and the corresponding compound, alexidine, having 2-ethylhexyl groups instead of chlorophenyl groups and other bis-biguanides such as those described in German patent application No. P 2,332,383 published Jan. 10, 1974, which sets forth the following formula:

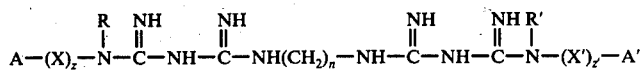

in which A and A' signify as the case may be either (1) a phenyl radical, which as substituent can contain up to 2 alkyl or alkoxy groups with 1 up to about 4C-atoms, a nitro group or a halogen atom, (2) an alkyl group which contains 1 to about 12C-atoms, or (3) alicyclic groups with 4 to about 12C-atoms, X and X' as the case may be may represent an alkylene radical with 1-3C-atoms, and z and z' are as the case may be either zero or 1, R and R' as the case may be may represent either hydrogen, an alkyl radical with 1 to about 12C-atoms or an aralkyl radical with 7 to about 12C-atoms, $n$ is a whole number of 2 to inclusively 12 and the polymethylene chain $(CH_2)_n$ can be interrupted by up to 5, ether, thioether, phenyl- or naphthyl groups; these are available as pharmaceutically suitable salts. Additional substituted guanidines are: N'-(4-chlorobenzyl)-$N^5$-(2,4-dichlorobenzyl) biguanide; p-chlorobenzyl biguanide, 4-chlorobenzhydryl guanylurea; N-3-lauroxypropyl-$N^5$-p-chlorobenzyl biguanide; 5,6-dichloro-2-guanidobenzimidazole; and N-p-chlorophenyl-$N^5$-laurylbiguanide.

The long chain tertiary amines also possess antibacterial and antiplaque activity. Such antibacterial agents include tertiary amines having one fatty alkyl group (typically 12 to 18 carbon atoms) and 2 poly(oxyethylene) groups attached to the nitrogen (typically containing a total of from 2 to 50 ethenoxy groups per molecule) and salts thereof with acids and compounds of the structure:

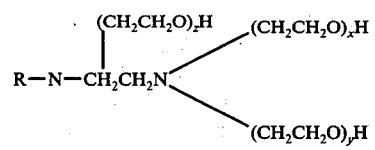

where R is a fatty alkyl group containing 12 to 18 carbon atoms and $x$, $y$ and $z$ total 3 or higher, as well as salts thereof. Generally, cationic agents are preferred for their antiplaque effectiveness.

The antibacterial antiplaque compound is preferably one which has a antibacterial activity such that its phenol coefficent is well over 50, more preferably well above 100, such as above about 200 or more for S. aureus; for instance the phenol coefficient (A.O.A.C.) of benzethonium chloride is given by the manufacturer as 410, for S. aureus. The cationic antibacterial agent will generally be a monomeric (or possibly dimeric) material of molecular weight well below 2,000, such as less than about 1,000. It is, however, within the broader scope of the invention to employ a polymeric cationic antibacterial agent. The cationic antibacterial agent is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The cationic antibacterial agents and long chain tertiary amine antibacterial agents effectively promote oral hygiene, particularly by removing plaque. However, their use has been observed to lead to staining of dental surfaces or discoloration.

The reason for the formation of such dental stain has not been clearly established. However, human dental enamel contains a high proportion (about 95%) of hydroxyapatite which includes $Ca^{+2}$ and $PO_4^{-3}$ ions. In the absence of dental plaque additional $Ca^{+2}$ and $PO_4^{-3}$, particularly from saliva, can be deposited on the enamel and such deposits can include color bodies which ultimately stain the tooth enamel as a calcified deposit thereon. It can be that as the cationic or long chain tertiary amine antibacterial agents remove plaque they also denature protein from saliva in the oral environment and the denatured protein can then act as a nucleating agent which is deposited on and stains or discolors tooth enamel.

Previously employed additives which reduced dental staining by cationic antibacterial antiplaque agents also generally reduced the activity of the antibacterial agents or its ability to act on dental plaque to measurable degrees. Further Victamide (also known as Victamine C) which is the condensation product of ammonia with phosphorus pentoxide actually increases staining even in the absence of a cationic antibacterial antiplaque agent and it and other known phosphorus containing agents such as disodium-ethane-1-hydroxy-1,1,-diphosphonic acid salt precipitate in the presence of antibacterial agent such as bis-biguanido compound, thereby reducing the antiplaque effectiveness of the antibacterial agent.

It is an advantage of this invention that an anti-nucleating additive is provided which prevents staining of dental enamel without substantially adversely affecting antibacterial and antiplaque activity of a cationic or long chain tertiary amine antibacterial agent. The anti-nucleating additives inhibit nucleation initiated by protein. Other advantages will be apparent from consideration of the following disclosure.

In accordance with certain of its aspects this invention relates to an oral composition comprising an oral vehicle, a nitrogen-containing cationic or long chain tertiary amine antimicrobial agent and a water soluble polymeric polyphosphomic compound selected from the group consisting of polymers having the recurring groups:

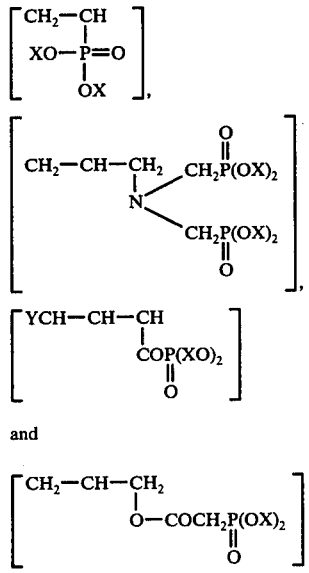

wherein X is selected from the group consisting of hydrogen and an orally acceptable cation and Y is selected from the group consisting of hydrogen and $CH_3$, and the unphosphonated recurring groups of compounds (1) and (3) have a molecular weight of at least about 3,500 and compounds (2) and (4) have a molecular weight of at least about 2,000. Typical orally acceptable cations include alkali metal (e.g. sodium and potassium), ammonium, $C_1$-$C_{18}$ mono-, di and tri-ethanolammonium cations.

The end groups of the polymers are typically the phosphonated or unphosphonated monomers thereof.

The molecular weight of the polymers, their total recurring groups and the unphosphonated forms thereof can be determined by various techniques including measurement of intrinsic viscosity.

Antibacterial agents which are cationic or long chain amine germicides which may be employed in the practice of this invention are described above. They are typically employed in amounts such that the oral product contains between about 0.001% and 15% by weight of the agent. Preferably for desired levels of antiplaque effect, the finished oral product contains about 0.01 to about 5%, and most preferably about 0.025% to 1.0% by weight of the agent. These amounts refer to the quantity of the free base form of the agent.

The stain which generally occurs on dental enamel is unexpectedly prevented when the polymeric polyphosphonic compound is employed. These materials are anti-nucleating agents. In themselves (even in the absence of antiplaque antibacterial agent) they are effective to reduce formation of dental calculus without unduly decalcifying enamel. However, not all anti-nucleating agents are effective to prevent stain by cationic antibacterial agents. For instance, Victamide actually increases staining even in the absence of an antibacterial antiplaque agent.

The polymeric polyphosphonated compounds having the recurring group

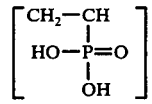

and orally acceptable salt thereof, are polymeric polyphosphonated polyethylene compounds wherein the polyethylene molecular weight is at least about 3,500 and typically about 3,500 to about 30,000 or more. Such polymers in the acid form have molecular weights of at least about 8,000 and typically about 8,060 to 61,500 or more. In the form of the sodium salts the molecular weights are at least about 10,000 and typically about 10,600 to 79,500 or more.

A desirable polymeric polyphosphonated polyethylene is characterized as having a polyethylene molecular wieght of about 30,000, a molecular weight in its acid form of about 61,500 and a molecular weight in its sodium form of about 79,500. The polyphosphonate polymer of the polyethylene Tenite 800 available from Eastman Kodak is such a polymer. It is made by reacting the polyethylene Tenite 800 with phosphoryl trichloride, hydrolyzing the product and converting to the salt form (e.g. sodium) if desired. Such a reaction is described by Anbar et al in the "Journal of Dental Research", Volume 53, No. 4, pages 867-878 (July-August, 1974).

Another desirable polymeric polyphosphonated polyethylene is characterized as having a polyethylene molecular weight of about 3,500, a molecular weight in its acid form of about 8,060 and a molecular weight in its sodium form of about 10,600. The polyphosphonate polymer of the polyethylene having an 11 methylene chain groups available from Union Carbide as DYDH is such a polymer. It is made in the same manner as the polyphosphonate polymer described above, except the polyethylene DYDH is used in place of Tenite 800. A phosphonate group is present on every 12th methylene carbon.

It is noteworthy that if the sodium salt polymer employed is the polyphosphonate of polyethylene having a 10 methylene chain, in which a phosphonate group is present on every 11th methylene carbon, in which the polyethylene molecular weight is about 3,000 and the acid form of which has a molecular weight of about 9270, the activity of a mouthwash containing an antibacterial antiplaque agent is diminished. When the molecular weight is greater, such activity is not diminished and stain can be reduced.

The polymeric allyl bis(phosphonomethylene) amine having the recurring group

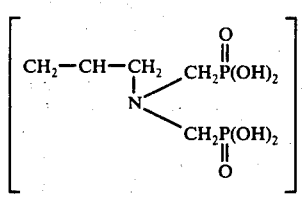

and salt thereof is made by direct reaction of allyl amine, formaldehyde and phosphorous acid ($H_3PO_3$) and converting to the salt form (e.g. sodium) if desired. The reaction is described in the "Journal of Organic Chemistry", Moedritzer et al, Volume 31, page 1603 et seq. (1966). A typical polymer is characterized by a molecular weight of the total polymer compound of at least about 2,000; the molecular weight of about 2,000 for the sodium salt being particularly desirable.

The polymeric acryloylphosphonic acid and methacryloylphosphonic acid having the recurring group

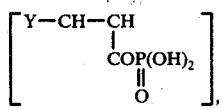

wherein Y is hydrogen or methyl, and salt thereof is made by phosphorylating an aqueous solution of polyacrylic or polymethacrylic acid with phosphoryl trichloride to form a rubber-like gel and converting to the salt form (e.g. sodium) if desired. The reaction is typically described in British Pat. No. 940,138 of Henkel & Cie. A particularly desirable polymer is characterized by a molecular weight of the unphosphonated methacrylic polymer of about 50,000; the degree of phosphonation being about 15-16%.

The polymeric polyallyl phosphonoacetate having the recurring group

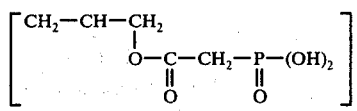

and salt thereof is made by reacting by the Arbuzov reaction, ethyl chloracetate ($ClCH_2COOC_2H_5$) with triethyl phosphite ($P(OC_2H_5)_3$) to form methylphosphonoacetate which on hydrolysis yields polyphosphonic acid

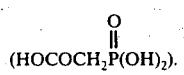

This is then chlorinated (to form

with thionyl chloride ($SO_2Cl_2$) in accordance with the reaction described in the "Journal of Organic Chemistry", Balsinger et al, Vol. 24, pages 434 et seq. (1959). Allyl alcohol ($CH_2=CHCH_2OH$) is then reacted with the chlorinated phosphonoacetic acid to form the allylphosphonoacetate monomer

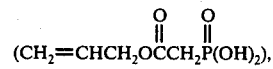

which is polymerized. The acid can be converted to the salt form (e.g. sodium), if desired. A typical polymer is characterized as having a total molecular weight of the polymeric compound of at least about 2,000; the molecular weight of about 2,000 for the sodium salt being particularly desirable.

The polymeric polyphosphonic compound which is most preferred is the polyallyl bis(phosphonomethylene) amine and particularly the sodium salt thereof. Such a polymer in its sodium form most preferably has a total molecular weight of about 2,000.

The concentration of polymeric polyphosphonic compound in the oral compositions can range widely, typically upward from about 0.01% by weight. There is no upper limit on the amount that can be utilized except as dictated by cost or incompatibility with the vehicle. Generally, concentrations from about 0.01% to about 10% by weight are utilized. Preferably polymeric polyallylphosphonoacetate is used in amounts upward from about 0.2%. Oral compositions which in the ordinary course of usage could be accidentally ingested preferably contain lower concentrations of polymeric polyphosphonic compounds. Thus, a mouthwash in accordance with this invention preferably contains less than 3% by weight of polymeric polyphosphonic compound. Dentifrice compositions, topical solutions and prophylactic pastes, the latter to be administered professionally, can contain from 0.01% to 10% by weight, preferably from 0.1% to 5% by weight of polymeric polyphosphonic compound. Most desirably, the polymeric polyphosphoric compound is present in a molar excess to the amount of antibacterial antiplaque agent (based on the free base thereof), in order to best prevent staining by the antibacterial antiplaque agent.

In certain highly preferred forms of the invention the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70% to about 99.9% by weight of the preparation. The pH of such liquid preparations is generally in the range of from about 4.5 to about 10 and typically from about 5.5 to 9.7. The pH is preferably in the range of from about 7 to about 9.2. It is noteworthy that the composition of the invention permits the use of the polymeric polyphosphic compound at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as a toothpowder, a dental tablet or a toothpaste or dental cream. Such compositions typically have a pH like that of a mouthwash or mouthrinse. The vehicle of such solid or pasty oral preparations contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 cm$^2$/gm. silica gel, complex amorphorus alkali metal aluminosilicate and hydrated alumina.

Alumina, particularly the hydrated alumina sold by Alcoa as C-333, which has an alumina content of 64.9% by weight, a silica content of 0.008%, a ferric oxide content of 0.003%, and a moisture content of 0.37% at 110° C., and which has a specific gravity of 2.42 and a particle size such that 100% of the particles are less than 50 microns and 84% of the particles are less than 20 microns, is particularly desirable.

When visually clear gels are employed, a polishing agent of collodial silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium tri-metaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amounts ranging from about 20% to about 99% by weight of the oral preparation. Preferably, it is present in amounts ranging from about 20% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In pasty oral preparations the combination of the antibacterial antiplaque agent and polymeric polyphosphonic compound should be compatible with the other components of the preparation. Thus, in a toothpaste, the liquid vehicle may comprise water and humectant typically in an amount ranging from about 10% to about 90% by weight of the preparation. Glycerine, sorbitol, or polyethylene glycol may also be present as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gum-like materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to about 10, generally about 5.5 to about 9.7 and preferably about 7 to about 9.2, may also contain a surface active agent and/or a fluorine-providing compound.

It will be understood that, as is conventional, the oral preparations are to be sold or otherwise distributed in suitably labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g. to promote foaming. It will be understood that it is preferable to employ nonionic surfactants rather than their anionic counterparts. Examples of water-soluble nonionic surfactants are condensation products of ethyleneoxide with various compounds reactive therewith having long hydrophobic chains (e.g. aliphatic chains of 12 to 20 carbon atoms) which condensation products ("ethoxamers") have hydrophobic polyoxyethylene moieties, such as condensation products of ethylene oxide and fatty acids, fatty alcohols, fatty amides, including alcohols such as sorbitan monostearate or polypropyleneoxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannous fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as a toothpaste or toothpowder, an amount of such compound which releases a maximum of 1% by weight of the preparation is considered satisfactory. Any suitable minimum amount of such compound may be used, but it is preferable to employ sufficient compound to release from 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight, more typically 0.76%.

In a liquid oral preparation such as a mouthwash, the fluorine-providing compound is typically present in an amount sufficient to release up to 0.13%, preferably from 0.0013% to 0.1% and most preferably from 0.0013% to 0.05%, by weight, of fluoride ion.

Various other materials may be incorporated in the oral preparations of this invention. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and saccharin. Suitably, flavor and sweetening agents may together comprise from 0.01% to 5% or more of the preparation.

Oral preparations of the invention may be prepared by dispersing the antibacterial antiplaque agent and the polymeric polyphosphonic compound in an oral vehicle which typically includes water.

For instance, a mouthrinse or mouthwash may be prepared by mixing ethanol and water with flavoring oil, nonionic surfactant, humectant, antibacterial antiplaque agent, such as benzethonium chloride or chlorhexidine, sweetener and color and then adding the polymeric polyphosphonic compound and additional water as desired. It is desirable to add the polymeric polyphosphonic compound after the other ingredients are contacted with each other.

A toothpaste may be prepared by forming a gel with humectant, gum or thickener such as hydroxyethyl cellulose, sweetener and adding thereto polishing agent, flavor, antibacterial antiplaque agent, such as benzethonium chloride or chlornexidine, and additional water, followed by addition of flavoring oil and the polymeric polyphoosphonic compound. It is preferable to add the polymeric polyphosphonic compound after the other components are contacted with each other. If sodium carboxymethyl cellulose and a bis-biguanido hexane antibacterial agent are employed as the gelling agent the procedure of either U.S. Pat. No. 3,842,168 or U.S. Pat. No. 3,843,779, modified by the inclusion of the polymeric polyphosphonic compound, is followed.

In the practice of this invention an oral composition such as a mouthwash or toothpaste containing cationic or long chain amine antibacterial antiplaque agent in amount effective to promote oral hygiene and polymeric polyphosphonic compound in amount effective to reduce staining of dental surfaces otherwise resulting from the presence of the antibacterial antiplaque agent is applied regularly to dental enamel, preferably from about five times per week to about three times daily.

The following specific examples are further illustrative of the nature of the present invention; but it is understood that the invention is not limited thereto. The compositions are prepared in the usual manner and all amounts of the various ingredients are by weight unless otherwise indicated.

EXAMPLE 1

The following mouthwash(a) is prepared:

|  | Parts |
|---|---|
| Flavored alcohol | 15 |
| Pluronic F-108 | 3 |
| Glycerine | 10 |
| Benzethonium chloride | 0.1 |
| Sodium saccharin | 0.03 |
| Polyallyl bis(phosphonomethylene) amine | 0.1 |
| Water | Q.S. to 100 |
| pH 7.7 | |

The polyallyl bis(phosphonomethylene) amine contains the recurring group

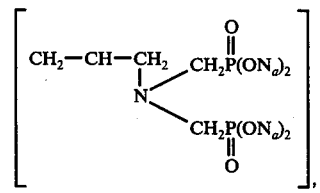

the molecular weight of the sodium salt of which is about 2,000.

The several ingredients are mixed with polyallyl bis(phosphonomethylene) amine with about 10 parts of water being withheld until the end.

Additional mouthwashes are prepared with the following modifications:

| Mouthwash | Parts of Benzethonium Chloride | Parts of Polyallyl Bis(phosphonomethylene) Amine | pH |
|---|---|---|---|
| (b) | 0.075 | 0.15 | 8.9 |
| (c) | 0.075 | 0.2 | 9.5 |
| (d) | 0.15 | 0.4 | 9.7 |

All compositions are clear without visible evidence of precipitation.

The antiplaque activity and staining levels of the mouthwashes of the same pH and composition except for the absence of the polyallyl bis(phosphonomethylene) amine are determined.

Tests are made of the ability of the compositions to inhibit in vitro plaque formation by allowing plaque to form (for 48 hours at 37° C.) on the surfaces of cleaned and pumiced teeth in a preinoculated sucrose broth containing *Strep mutans*. The pre-grown plaque is then immersed in the test composition and rinsed with a buffer 1–5 times for 1 minute each. The teeth carrying the plaque are then transferred to a sucrose broth containing 1 mg/100 ml of bromocresol green indicator and incubated at 37° C. anaerobically for 18 hours. An antibacterial compound is considered effective if the indicator does not turn yellow (which begins when pH reaches 5.5) and there is no further growth of the plaque as judged by the increase in turbidity. It is found that on the clean teeth, plaque formation and plaque growth are effectively inhibited.

The tooth staining characteristics of the composition are tested by slurrying hydroxylapatite with salivary protein and acetaldehyde and a pH 7 phosphate buffer. The mixture is shaken at 37° until a light brown color is formed, which colored material is separated.

Color levels are determined on a Gardner Color Difference Meter before and after the test composition is applied to the colored material.

The antiplaque results are as follows:

| Composition | | Active After Indicated No. Of Rinses With Buffer | Inhibition of Three Day Plaque Growth & Acid Production | |
|---|---|---|---|---|
| | Polymeric Phosphonate Presence | | Growth | Acid |
| (a) | no | 5 | yes | yes |
| (a) | yes | 5 | yes | yes |
| (b) | no | 5 | yes | yes |
| (b) | yes | 5 | yes | yes |
| (c) | no | 5 | yes | yes |
| (c) | yes | 5 | yes | yes |
| (d) | no | 5 | yes | yes |
| (d) | yes | 5 | yes | yes |

Thus, it is observed that the polyallyl bis(phosphonomethylene) amine does not reduce the in vitro antiplaque activity of benzethonium chloride.

The antistain results are as follows for the mouthwashes of the invention and corresponding mouthwashes from which the polymeric polyphosphonic compound is omitted:

| Mouthwash | | | |
|---|---|---|---|
| | Polymeric Polyphosphonic Compound Presence | Reflectance | Reflectance Difference |
| (a) | no | 46 | |
| (a) | yes | 51 | 5 |
| (b) | no | 57 | |
| (b) | yes | 72 | 15 |
| (c) | no | 54 | |
| (c) | yes | 64 | 10 |
| (d) | no | 51 | |
| (d) | yes | 68 | 17 |

In the cases of mouthwashes (b), (c) and (d), each with and without polymeric polyphosphonic compound additive, the pH is adjusted to 8 with hydrochloric acid after preparation in order to render the pH values uniform.

Thus, it is observed that the polyallyl bis(phosphonomethylene) amnine substantially reduces staining by benzethonium chloride particularly at a pH of about 8.

EXAMPLE 2

Mouthwashes similar to those of Example 1 are prepared except that chlorhexidine diacetate and chlorhexidine digluconate in amount corresponding to 0.1 part of chlorhexidine free base and the polyallyl bis(phosphonomethylene) amine are present and the pH is adjusted below 8. These mouthwashes are active against plaque in vitro and inhibit plaque growth and acid as do the corresponding mouthwashes without the polyallyl bis(phosphonomethylene) amine. In the antistain test the stain levels when the polymeric polyphosphonic compound is present is less than the stain level when it is absent.

Alexidine also maintains its antiplaque effect with reduced staining in the presence of the polyallyl bis(phosphonmethylene) amine, as do other antibacterial antiplaque agents including cetyl pyridinium chloride and a $C_{12}$–$C_{18}$ alkyl tertiary amine of the formula:

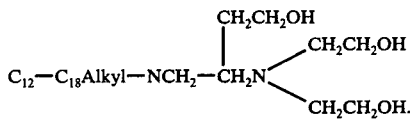

EXAMPLE 3

Mouthwashes corresponding to those of Example 1 with the indicated amounts of benzethonium chloride and the indicated amounts of particular polymeric polyphosphonic compound in place of polyallyl bis(phosphonomethylene) amine are prepared:

| | Parts of Benzethonium Cholride | Parts of Polymeric Polyphosphonic Compound | Polymeric Polyphosphonic Compound | pH |
|---|---|---|---|---|
| (a) | 0.1 | 0.1 | * | 9.2 |
| (b) | 0.075 | 0.15 | * | 9.4 |
| (c) | 0.075 | 0.2 | * | 9.5 |
| (d) | 0.15 | 0.4 | * | 9.4 |
| (e) | 0.1 | 0.1 | ** | 8.4 |
| (f) | 0.075 | 0.15 | ** | 7.9 |
| (g) | 0.075 | 0.2 | ** | 8.3 |
| (h) | 0.15 | 0.4 | ** | 8.0 |
| (i) | 0.1 | 0.1 | *** | 7.7 |
| (j) | 0.075 | 0.2 | *** | 8.5 |
| (k) | 0.15 | 0.4 | *** | 8.4 |
| (l) | 0.1 | 0.1 | **** | 8.4 |
| (m) | 0.075 | 0.15 | **** | 8.5 |
| (n) | 0.075 | 0.2 | **** | 8.4 |

-continued

| Parts of Benzethonium Choloride | Parts of Polymeric Polyphosphonic Compound | Polymeric Polyphosphonic Compound | pH |
|---|---|---|---|
| (o) 0.15 | 0.4 | **** | 8.5 |

*is a polymeric polyphosphonic compound having the recurring group 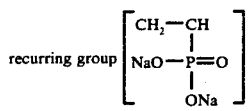

wherein the polyethylene molecular weight is about 3,500 and the total molecular height is about 10,600.
**is the polymeric polyphosphonic compound having the recurring group 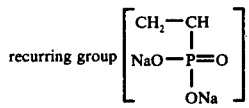

wherein the polyethylene molecular weight is about 30,000 and the total molecular weight is about 79,500.
***is the polymeric polyphosphonic compound having the recurring group 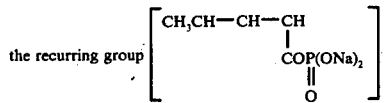

wherein the unphosphonated molecular weight is about 50,000 and the degree of phosphonation is about 15.52%.
****is the polymeric polyphosphonic compound having the recurring group 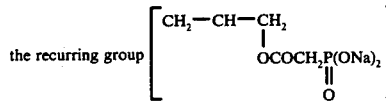

wherein the polymeric molecular weight is about 2,000. These mouthwashes are active against plaque in vitro and inhibit three day plaque growth and acid as do the corresponding mouthwashes without the polymeric polyphosphonic compound.

The following results are observed in the antistain test for the mouthwashes and corresponding mouthwashes from which the polymeric polyphosphonic compound is omitted:

| Mouthwash | Polymeric Polyphosphonic Compound Presence | Reflectance | Reflectance Difference |
|---|---|---|---|
| (a) | No | 46 | |
| (a) | Yes | 57 | 11 |
| (b) | No | 57 | |
| (b) | Yes | 57 | 0 |
| (c) | No | 54 | |
| (c) | Yes | 57 | 3 |
| (d) | No | 51 | |
| (d) | Yes | 57 | 6 |
| (e) | No | 46 | |
| (e) | Yes | 50 | 4 |
| (f) | No | 57 | |
| (f) | Yes | 57 | 0 |
| (g) | No | 54 | |
| (g) | Yes | 57 | 3 |
| (h) | No | 51 | |
| (h) | Yes | 59 | 8 |
| (i) | No | 46 | |
| (i) | Yes | 46 | 0 |
| (j) | No | 54 | |
| (j) | Yes | 57 | 3 |
| (k) | No | 51 | |
| (k) | Yes | 63 | 12 |
| (l) | No | 46 | |
| (l) | Yes | 46 | 0 |
| (m) | No | 57 | |
| (m) | Yes | 57 | 0 |
| (n) | No | 54 | |
| (n) | Yes | 60 | 6 |
| (o) | No | 51 | |
| (o) | Yes | 55 | 4 |

In those situations in which no substantial reflectance difference is observed (b, f, i, l and m) the pH is not adjusted after preparation of the mouthwashes. In all other situations, the pH was adjusted to 8.0 and stain is reduced.

EXAMPLE 3

The following antiplaque reduced staining toothpastes are prepared:

| | Parts | Parts |
|---|---|---|
| Hydrated Alumina | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Benzethonium chloride | 0.5 | — |
| Chlorhexidine digluconate (20%) | — | 4.725 |
| Polyallyl bis(phosphonomethylene) amine (of Example 1) | 2 | 2 |
| Sodium saccharin | 0.17 | 0.17 |
| Flavor | 0.8 | 0.8 |
| Water | Q.S. to 100 | Q.S. to 100 |

It will be apparent to one skilled in the art that modifications of the above examples may be made thereto.

I claim:

1. An oral composition comprising an oral vehicle, an amidine antibacterial antiplaque agent tending to stain dental surfaces and a water soluble polymeric polyphosphonic compound having the recurring group:

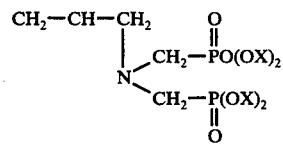

wherein X is selected from the group consisting of hydrogen and an orally acceptable cation and said compound antistain additive has a molecular weight of at least about 2,000.

2. The oral composition of claim 1 wherein said polymeric polyphosphonic compound is in the form of its sodium salt and has a molecular weight of about 2,000.

3. The oral composition of claim 1 wherein said antibacterial antiplaque agent is present in amount to provide about 0.001% to about 15% by weight based on the free base form of said agent and said polymeric polyphosphonic compound is present in amount of about 0.01% to about 10% by weight.

4. The oral composition of claim 3 whereim said antibacterial antiplaque agent is present in amount of about 0.01% to about 5% by weight based on the free base form of said agent and said polymeric polyphosphonic compound is present in a molar excess to said agent.

5. The oral composition of claim 3 wherein said antibacterial antiplaque agent is a substituted guanidine.

6. The oral composition of claim 5 wherein said antibacterial antiplaque agent is a pharmaceutically acceptable water soluble salt of an agent selected from the group consisting of chlorhexidine and alexidine.

7. The oral composition of claim 6 wherein said antibacterial antiplaque agent is a pharmaceutically acceptable water soluble salt of chlorhexidine.

8. The oral composition of claim 1 wherein said vehicle is an aqueous-alcohol and said composition is a mouthwash of pH of about 4.5 to about 10.

9. The oral composition of claim 1 wherein said vehicle comprises a liquid vehicle and a gelling agent and a dentally acceptable polishing material is present and said composition is a toothpaste of pH of about 4.5 to about 10.

* * * * *